United States Patent [19]

De Miniac

[11] Patent Number: 5,888,788
[45] Date of Patent: Mar. 30, 1999

[54] USE OF IONOPHORETIC POLYETHER ANTIBIOTICS FOR CONTROLLING BACTERIAL GROWTH IN ALCOHOLIC FERMENTATION

[75] Inventor: Michel De Miniac, Paris, France

[73] Assignee: Union Nationale des Groupements de Distillateurs d'Alcool (UNGDA), France

[21] Appl. No.: 558,667

[22] Filed: Nov. 16, 1995

Related U.S. Application Data

[63] Continuation of Ser. No. 245,576, May 18, 1994, abandoned, which is a continuation-in-part of PCT/FR92/00984 Oct. 20, 1992.

[51] Int. Cl.⁶ ............................................. C12P 7/06
[52] U.S. Cl. .................................. 435/161; 435/244
[58] Field of Search ...................... 435/161, 244

[56] References Cited

U.S. PATENT DOCUMENTS

| | | |
|---|---|---|
| 4,137,241 | 1/1979 | Liu et al. . |
| 4,138,496 | 2/1979 | Shibata et al. . |
| 4,293,650 | 10/1981 | Florent et al. . |
| 4,316,956 | 2/1982 | Lützen . |
| 4,359,583 | 11/1982 | Mizutani et al. . |
| 4,409,329 | 10/1983 | Silver . |
| 4,426,450 | 1/1984 | Donofrio . |
| 4,510,317 | 4/1985 | Liu et al. . |
| 5,043,353 | 8/1991 | Yao et al. . |
| 5,059,431 | 10/1991 | Daeschel et al. . |
| 5,100,791 | 3/1992 | Spindler et al. . |

FOREIGN PATENT DOCUMENTS

| | | |
|---|---|---|
| 2032598 | 11/1970 | France . |
| 2587035 | 8/1989 | France . |
| 197549497 | 5/1975 | Japan . |
| 840736 | 6/1981 | U.S.S.R. . |
| 881114 | 11/1981 | U.S.S.R. . |
| 2121821 | 1/1984 | United Kingdom . |

OTHER PUBLICATIONS

Henning et al., *Intl. J. Food Microbiol.* 3, 135–141 (1986).
Nagarja et al., *J. Animal Sci.* 65, 1064–1076, (1987).
Phillips et al., *J. Applied Bacteriology* 60, 491–500 (1986).
Kutas et al., *Chem. Abstracts* 97(23), 197321n (1982).

*Primary Examiner*—Irene Marx
*Attorney, Agent, or Firm*—McDonnell, Boehnen, Hulbert & Berghoff

[57] ABSTRACT

The addition of about 0.3 to about 3 ppm of at least one polyether ionophore antibiotic to a fermentation broth inhibits production of organic acids that hinder the growth and fermentation of yeast. The present invention is useful in a variety of feedstocks, including sugar beet juice, sugar cane juice, diluted sugar beet molasses, diluted sugar cane molasses, hydrolyzed grain (e.g., corn or wheat), hydrolyzed starchy tubers (e.g., potatoes or Jerusalem artichokes), wine, wine by-products, cider, and cider by-products.

16 Claims, 2 Drawing Sheets

USE OF IONOPHORETIC POLYETHER ANTIBIOTICS FOR CONTROLLING BACTERIAL GROWTH IN ALCOHOLIC FERMENTATION

BACKGROUND OF THE INVENTION

This is a continuation of application Ser. No. 08/245,576, filed May 18, 1994, now abandoned, which is a continuation-in-part of International Application No. PCT/FR92/00984, filed Oct. 20, 1992.

1. Field of the Invention

This invention relates to the use of polyether ionophore antibiotics to control bacterial growth in alcohol (ethanol) fermentation broths.

2. Description of the Art

Alcohol fermentation plants typically do not operate under sterile conditions and can harbor bacterial populations that can reach $10^4$ to $10^6$ organisms/ml, or even more in extreme cases. These microorganisms often belong to the lactobacillus genus, but can also include other types such as streptococcus, bacillus, pediococcus, clostridium or leuconostoc (see Table 1).

TABLE 1

TYPICAL BACTERIA ENCOUNTERED
IN ALCOHOL FERMENTATION PLANTS

Lactobacillus buchneri
Lactobacillus plantarum
Lactobacillus casei alactosus
Lactobacillus casei casei
Lactobacillus brevis 2
Lactobacillus brevis 3
Lactobacillus acidophilus
Lactobacillus fermentum
Lactobacillus lindnerii
Leuconostoc mesenteroides
Streptococcus equinus
Pediococcus pentosaceus
Bacillus pumilus
Bacillus cereus
Clostridium butyricum These bacteria are all capable of producing organic acids. When the population exceeds $10^6$ organisms/ml, production of organic acids can become significant. At concentrations greater that 1 g/l these organic acids can hinder the growth and fermentation of yeast and cause the productivity of the plant to drop by 10–20% or more.

With certain feedstocks, such as wine, cider, or their by-products, these bacteria can also degrade glycerol into acrolein, a cancer causing substance that can end up in alcohol products intended for human consumption.

Consequently, bacteriostatic and/or bactericidal methods that do not adversely affect fermentation are needed to prevent the detrimental effects caused by excessive growth of bacteria in fermentation media.

SUMMARY OF THE INVENTION

The object of the present invention is to combat the detrimental effects to fermentation media resulting from excessive growth of bacteria. The present invention achieves this objective by providing a method that stunts bacterial growth and/or kills the bacteria. The inventive method comprises introducing into a fermentation broth an effective bacteriostatic or bactericidal quantity of a polyether ionophore antibiotic. The method of the present invention is contemplated as being useful with a wide variety of fermentation broths, including feedstocks such as sugar beet juice, sugar cane juice, diluted sugar beet molasses, diluted sugar cane molasses, hydrolyzed grain (e.g., corn or wheat), hydrolysed starchy tubers (e.g., potatoes or Jerusalem artichokes), wine, wine by-products, cider, and cider by-products. Thus, any starch or sugar-containing material that can be fermented with yeast to yield alcohol (ethanol) can be utilized in accordance with the present invention. The resulting bacterial control eliminates or greatly reduces the problems caused by the bacteria and the organic acids they produce. The polyether ionophores useful in the present invention have no adverse effect on the yeast (saccharomices sp.) or the fermentation process.

DESCRIPTION OF THE PREFERRED EMBODIMENTS

Figure 1:
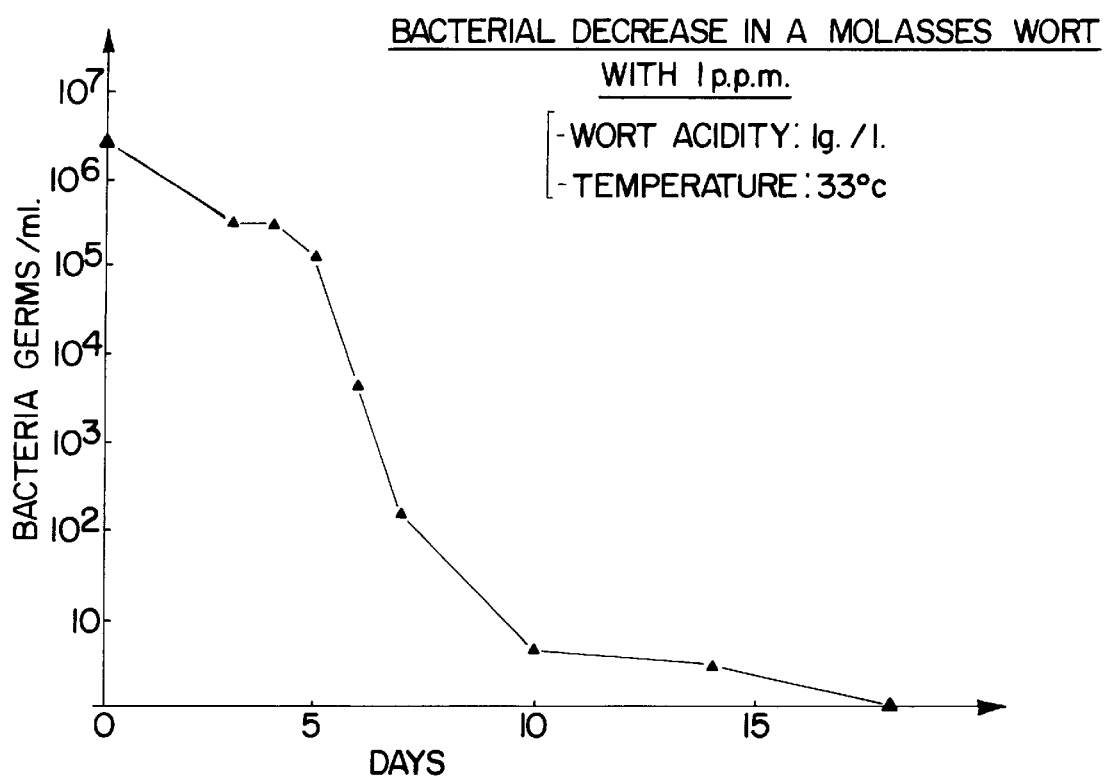
FIG. 1 displays the decline of bacterial population of diluted molasses juice after the addition of monensin.

The present invention comprises introducing into a sugar containing fermentation medium an effective bacteriostatic or bactericidal amount (for example, about 0.5 ppm) of a polyether ionophore antibiotic that has a bacteriostatic and/or bactericidal action. That is to say, the polyether ionophore prevents or inhibits the bacteria in the fermentation medium from growing but has no effect on the yeast up to a concentration of about 100 ppm. The bacterial flora can thereby be maintained at a concentration of $10^4$/ml or less, resulting in essentially no production of organic acidity. Hence, the bacteria are unable to slow down alcoholic fermentation to any significant extent. Under these conditions, the bacteria typically cannot produce acrolein either. At doses of about 0.5 ppm, the antibiotic has a bactericidal action and hence makes it possible to achieve a decline in bacterial content.

Polyether ionophore antibiotics are very stable compounds. They do not easily degrade over time or under high temperatures. This is valuable for fermentation plants since:

1. they remain active for many days under typical fermentation plant operating conditions; and
2. they remain active at the high temperatures encountered during the enzymatic hydrolysis of starch that precedes the fermentation of grain or tubers (for example, 2 hours at 90° C. or 1.5 hours at 100° C.).

These compounds are commercially available from pharmaceutical supply firms.

We conducted experiments with several polyether ionophore antibiotics, such as monensin, lasaalosid, and salinomycin, using fermentation feedstocks derived from sugar beet molasses. These experiments confirmed the existence of bacteriostatic and bactericidal concentrations that range from approximately 0.5 ppm to about 1.5 ppm. At bacteriostatic concentrations, the growth of the bacterial population stops and no increase in the production of organic acids can be measured. At bactericidal concentrations, the bacterial population drops and, consequently, no increase in the production of organic acids can be measured.

The method of the present invention comprises addition to a fermentation medium of an effective bacteriostatic or bactericidal amount of at least one polyether ionophore antibiotic. In a preferred embodiment, the present invention comprises introducing into a fermentation medium at least one polyether ionophore antibiotic in a concentration of from about 0.3 to about 3 ppm. In a particularly preferred embodiment, the concentration of the polyether ionophore antibiotic added is from about 0.5 to about 1.5 ppm.

The polyether ionophore antibiotics useful in the present invention are any of those that do not substantially affect the yeast and that have bacteristatic and/or bactericidal effects on fermentation broth bacteria that produce organic acids. Among the polyether ionophore antibiotics contemplated as useful in the present invention are those that are effective against the bacterial recited in Table 1, supra. The preferred polyether ionophore antibiotics are monensin, lasalosid, salinomycin, narasin, maduramycin, and semduramycin. Monensin, lasalosid, and salinomycin are particularly preferred, while monensin is the most preferred.

Fermentation broths that may be effectively treated with the methods of the present invention include feedstocks such as, for instance, sugar beet juice, sugar cane juice, diluted sugar beet molasses, diluted sugar cane molasses, hydrolyzed grain (e.g., corn or wheat), hydrolysed starchy tubers (e.g., potatoes or Jerusalem artichokes), wine, wine by-products, cider, and cider by-products. Thus, any starch or sugar containing material that can be fermented with yeast to yield alcohol (ethanol) can be utilized in accordance with the present invention.

The following examples are intended for illustrative purposes and are not intended and should not be construed as limiting the invention in any way.

EXAMPLE

Example 1
Impact of Monensin on the Concentration of *Lactobacillus buchneri*

Varying concentrations of monensin were added to sugar beet molasses derived fermentation feedstocks, and the acidity and bacterial concentration were measured. The results are presented in Table 2.

Example 2
Stability and Bacterial Effect of Monensin in Molasses Juice 1 ppm of monensin was introduced into diluted molasses juice containing $10^6$ bacteria/ml. FIG. 1 shows the decline of the bacterial population over 20 days at 33° C. There is no resumption of growth at any time. This shows that monensin remains active for at least 20 days at 33° C. under normal fermentation plant operating conditions.

Example 3
Large Scale Use of Monensin

Figure 2:
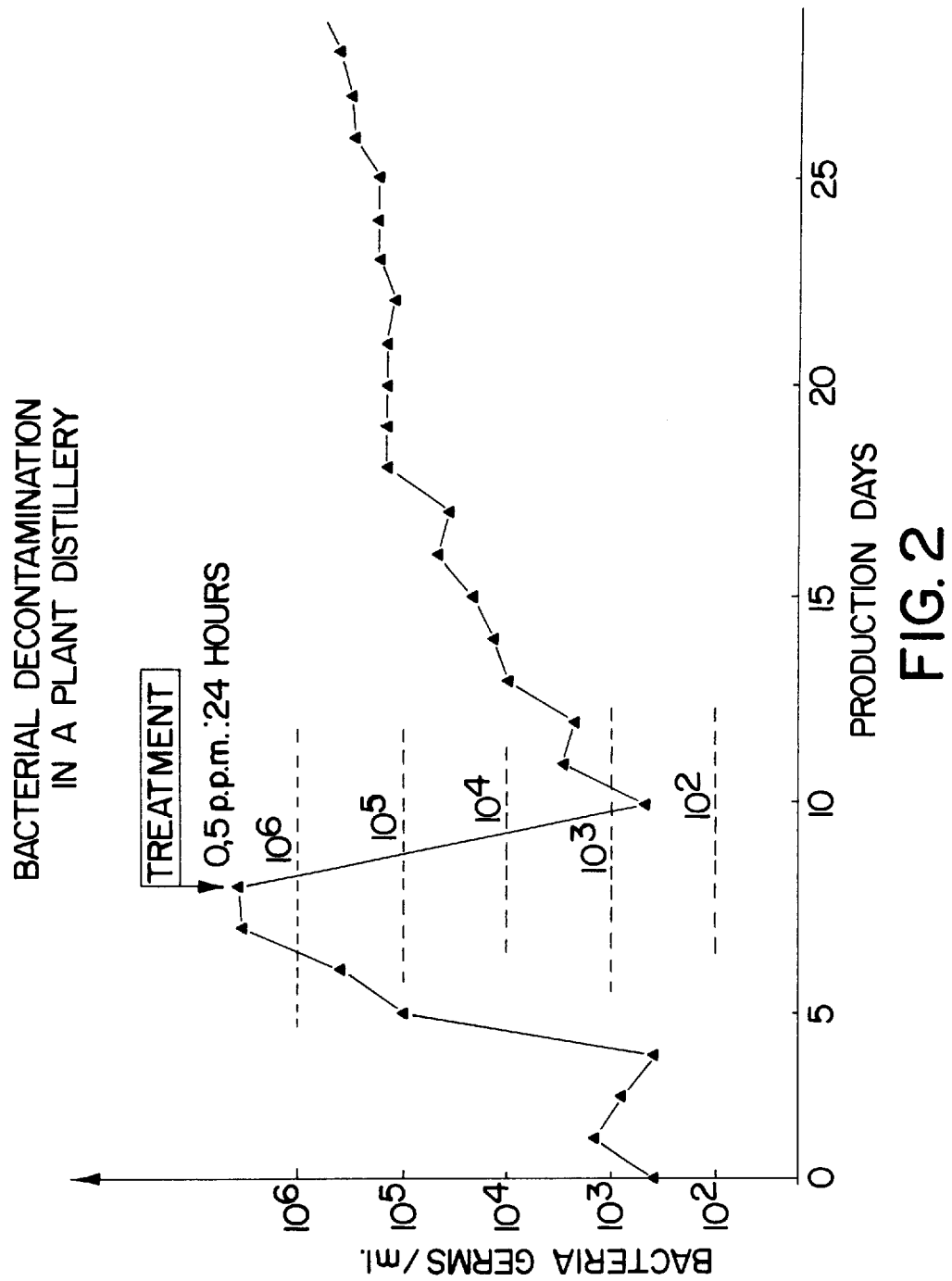
FIG. 2 displays the effect of addition of monensin on the bacterial population in a continuous process commercial scale fermentation plant.

A further example of the invention is illustrated in FIG. 2. It relates to an alcohol fermentation plant that operated with a continuous process. The fermentation broth was a molasses must comprising 14% sugar (about 300 g/l). The flow rate was 40 to 50 $m^3$/hr, and the temperature was 33° C. On day 7, contamination reached in excess of $10^6$ organisms/ml. On day 8, treatment was begun with the introduction of an active quantity of monensin (dissolved in ethanol) in the fermenter. This concentration of monensin was maintained for 24 hours with the addition of a food stock enriched with a similar concentration of monensin. On day 9, the addition of monensin to the feed stocks stopped. Immediately after the treatment began, the bacterial population began to drop rapidly. This decline continued until day 10, that is 24 hours after the end the treatment. At this stage, monensin was eliminated from the fermentation broth, and bacterial growth resumed slowly. It remained manageable for the next 15 days, however, because of the reduced contamination level following treatment.

I claim:

1. A method of controlling bacterial growth in an alcoholic fermentation medium comprising adding to the fermentation medium from about 0.3 to 3 ppm of a polyether ionophore, wherein the alcoholic fermentation medium is a starch or sugar-containing feedstock fermented with yeast to yield alcohol.

2. A method according to claim 1 wherein the feedstock is selected from the group consisting of sugar beet juice, sugar cane juice, diluted sugar beet molasses, diluted sugar cane molasses, hydrolyzed grain, hydrolyzed starch tubers, and cider.

3. A method according to claim 2 wherein the polyether ionophore antibiotic is selected from the group consisting of monensin, lasalosid, salinomycin, narasin, maduramycin, and semduramycin.

4. A method according to claim 3 wherein the polyether ionophore antibiotic is monensin.

5. A method according to claim 1 wherein the polyether ionophore antibiotic is selected from the group consisting of monensin, lasalosid, salinomycin, narasin, maduramycin, and semduramycin.

6. A method of controlling bacterial growth in an alcoholic fermentation medium according to claim 1 comprising adding to the fermentation medium from about 0.5 to about 1.5 ppm of a polyether ionophore antibiotic.

7. A method according to claim 6 wherein the polyether ionophore antibiotic is selected from the group consisting of

TABLE 2

| INITIAL CONDITIONS Inoculum: $2 \times 10^6$ cells/ml Acidity: 1 g/l pH 5.6 | | | | | | | |
|---|---|---|---|---|---|---|---|
| Monensin concentration (ppm) | 0 | 0.5 | 1.0 | 1.5 | 2.0 | 2.5 | 3.0 |
| Bacterial count after 24 hours | $4 \times 10^6$ | $8 \times 10^5$ | $10^4$ | $<10^3$ | $2 \times 10^2$ | $2 \times 10^2$ | $2 \times 10^2$ |
| Bacterial count after 48 hours | $10^9$ | $2 \times 10^6$ | $2 \times 10^3$ | $<10^3$ | $<10^3$ | $<10^3$ | $<10^3$ |
| Acidity (g/l) | 5 | 1 | 1 | 1 | 1 | 1 | 1 |
| pH | 4.5 | 5.6 | 5.6 | 5.6 | 5.6 | 5.6 | 5.6 |
| Change in acidity (g/l) | 4.2 | 0 | 0 | 0 | 0 | 0 | 0 | monensin, lasalosid, salinomycin, narasin, maduramycin, and semduramycin.

8. The method according to claim 6 wherein the feedstock is wine.

9. The method according to claim 8 wherein the polyether ionophore antibiotic is selected from the group consisting of monensin, lasalocid, salinomycin, narasin, maduramycin, and semduramycin.

10. The method according to claim 9 wherein the polyether ionophore antibiotic is monensin.

11. A method according to claim 6 wherein the feedstock is selected from the group consisting of sugar beet juice, sugar cane juice, diluted sugar beet molasses, diluted sugar cane molasses, hydrolyzed grain, hydrolyzed starch tubers, and cider.

12. A method according to claim 11 wherein the polyether ionophore antibiotic is selected from the group consisting of monensin, lasalosid, salinomycin, narasin, maduramycin, and semduramycin.

13. A method according to claim 12, wherein the polyether ionophore antibiotic is monensin.

14. The method according to claim 1 wherein the feedstock is wine.

15. The method according to claim 14 wherein the polyether ionophore antibiotic is selected from the group consisting of monensin, lasalosid, salinomycin, narasin, maduramycin, and semduramycin.

16. The method according to claim 15 wherein the polyether ionophore antibiotic is monensin.

\* \* \* \* \*